United States Patent
Crane et al.

(10) Patent No.: US 6,230,046 B1
(45) Date of Patent: May 8, 2001

(54) SYSTEM AND METHOD FOR ENHANCED VISUALIZATION OF SUBCUTANEOUS STRUCTURES

(75) Inventors: Robert L. Crane, Kettering; Byron P. Edmonds, Beavercreek; Charles C. Lovett, Miamisburg; Walter E. Johnson, Dayton, all of OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 08/945,369

(22) PCT Filed: Apr. 18, 1996

(86) PCT No.: PCT/US96/05506

§ 371 Date: Oct. 20, 1997

§ 102(e) Date: Oct. 20, 1997

(87) PCT Pub. No.: WO96/36273

PCT Pub. Date: Nov. 21, 1996

Related U.S. Application Data

(63) Continuation-in-part of application No. 08/442,041, filed on May 16, 1995, now abandoned.

(51) Int. Cl.[7] ....................................................... A61B 6/00
(52) U.S. Cl. ........................... 600/476; 250/330; 250/372
(58) Field of Search .................................. 600/473, 476, 600/310; 250/214 VT, 214 LA, 574, 330, 342, 358.1, 363.01, 363.02, 365, 372, 461.1

(56) References Cited

U.S. PATENT DOCUMENTS

| | | | |
|---|---|---|---|
| 4,817,622 | * | 4/1989 | Pennypacker et al. ............... 600/473 |
| 5,241,170 | * | 8/1993 | Field, Jr. et al. ..................... 250/226 |
| 5,417,688 | * | 5/1995 | Elstrom et al. ......................... 606/64 |
| 5,519,208 | * | 5/1996 | Esparza et al. ....................... 250/226 |
| 6,032,070 | * | 2/2000 | Flock et al. ........................... 600/473 |

FOREIGN PATENT DOCUMENTS

| | | | |
|---|---|---|---|
| 4421237 | * | 6/1994 | (DE) . |
| 2276749 | * | 5/1994 | (GB) . |

* cited by examiner

Primary Examiner—Brian L. Casler
(74) Attorney, Agent, or Firm—Bobby D. Scearce; Thomas L. Kundert

(57) ABSTRACT

System and method for enhancing visualization of veins, arteries or other subcutaneous natural or foreign structures of the body and for facilitating intravenous insertion or extraction of fluids, medication or the like in the administration of medical treatment to human or animal subjects are described which comprise a light source (11) for illuminating or transilluminating the corresponding portion of the body with light of selected wavelengths and a low-level light detector (12) such as an image intensifier tube (including night vision goggles), a photomultiplier tube, photodiode or charge coupled device, for generating an image of the illuminated body portion, and optical filter(s) (17) of selected spectral transmittance which can be located at the light source(s) (11), detector (12), or both.

20 Claims, 10 Drawing Sheets

SYSTEM AND METHOD FOR ENHANCED VISUALIZATION OF SUBCUTANEOUS STRUCTURES

RELATED APPLICATION

This application is filed under 35 U.S.C. 371 of PCT/US96/05506 which is a continuation-in-part of U.S. application Ser. No. 08/442,041, filed May, 16, 1995, now abandoned.

TECHNICAL FIELD

The invention described herein relates generally to medical devices and procedures, and more particularly to a system and method for enhancing visualization of veins, arteries and other subcutaneous structures of the body for facilitating fluid insertion into or extraction from the body or otherwise visualizing subcutaneous structures for diagnosis of the medical condition of a patient or administration of medical treatment to a patient.

The invention described herein may be manufactured and used by or for the Government of the United States of America for all governmental purposes without the payment of any royalty.

BACKGROUND ART

Prior art devices and procedures for enhancing visualization of veins, arteries and other subcutaneous structures of the body have included the following techniques: applying tourniquets, flashlights, direct application of liquid crystalline materials, dual fiber optic sources, and ultrasonic imaging. The tourniquet technique is the traditional approach in which the venous return is restricted to cause the major superficial venous vessels to engorge with blood for enhancing their visibility. This is the standard approach used in all medical facilities. However, this technique is compromised in conditions of poor ambient illumination, and in patients with low blood pressure, skin burns, etc. Flashlights are limited to transilluminating very thin sections of tissue. The liquid crystal technique is based on the thermal sensitivity of liquid crystal materials. By applying a thin liquid crystal film over the vein, it is possible to map out the venous structure from the surrounding tissue based on relative temperature differences. The dual fiber-optic source is a method by which both sides of the venous structure are simultaneously illuminated with visible light to eliminate shadows and to provide enhanced visualization. Lastly, ultrasonic images can be taken of vascular and surrounding tissue. This technique is based on the reflection of ultrasonic waves due to the impedance mismatch at the various tissue interfaces found within the body.

In the administration of medical care in an emergency situation, such as that encountered by a physician or emergency medical technician (EMT) in the treatment of an accident victim at the scene of the accident, or by a medic in the treatment of the wounded on a battlefield, the conditions under which the care is administered may be adverse, such as nighttime lighting conditions. It is obvious and well settled that expeditious administration of medical care to the victim improves the prospects of recovery of the victim. For example, the life of a wounded soldier on the battlefield may depend on the immediate intravenous administration of blood plasma or other lost body fluids or of medications. Similar immediate procedures by a physician or EMT may be required in order to treat a victim at the scene of an accident. Further, during transport of the victim to a hospital or similar medical care facility, administration of medical procedures may be necessary under poor lighting conditions or under other adverse conditions (e.g., torn clothing, bleeding, etc) consequent of the accident. Additionally, shock may have caused the veins of the victim to partially collapse, or the patient may have veins which are difficult to find which further complicates procedures for gaining access to the veins or arteries of the victim.

Numerous background art references are cited throughout the Description of the Best Mode for Carrying out the Invention presented hereinbelow, which references have been incorporated herein by reference.

DISCLOSURE OF THE INVENTION

The invention solves or substantially reduces in critical importance problems with conventional systems and methods for visualizing subcutaneous structures of the body under poor lighting or other adverse conditions by providing system and method for illuminating or transilluminating a portion of the body with light of selected wavelength(s), in the ultraviolet (UV), visible or near infrared (NIR) (about 0.3 to 1.0 micron ($\mu$m)), and viewing the illuminated portion of the body with an image intensifier or other low-level light detection means, such as that included with conventional night vision goggles (NVG), whereby the vascular system (veins, arteries) of the body or other subcutaneous structure is visualized by reason of the difference in spectral absorption of the blood (or other subcutaneous structures) as compared to surrounding tissue. Intravenous insertion or extraction of body fluids or medication under nighttime or other darkened conditions is therefore facilitated, differentiation between arterial and venous blood may be made, treatment of patients in shock or surgical procedures on patients who have suffered blood loss or are without adequate venous structure may be facilitated, fibrous or cancerous tissues may be identifiable by reason of their structural/absorptive character, treatment of pediatric patients may be facilitated, and the enhanced collateral circulation associated with damaged tissues and the healing process and the formation of scar tissue may be detectable.

In accordance with the foregoing principles and objects of the invention, system and method for enhancing visualization of veins, arteries or other subcutaneous structures of the body and for facilitating intravenous insertion or extraction of fluids, medication or the like are described which comprise illuminating or transilluminating the corresponding portion of the body with light of selected wavelength and viewing the illuminated portion through a sensitive imaging sensor such as an imaging intensifier tube, intensified charge coupled display (CCD), a scanning photo multiplier tube (PMT), or photodiode, and optical filters of selected spectral transmittance which can be located between the various light sources and the sensor.

It is therefore a principal object of the invention to provide system and method for the non-invasive visualization or identification of subcutaneous structures of the body.

It is another object of the invention to provide system and method for detecting and mapping the veins and arteries in human subjects.

It is another object of the invention to provide system and method for visualization and identification of veins, arteries and other subcutaneous structures under adverse lighting conditions.

It is another object of the invention to provide a non-invasive means to visualize human body internal tissue for purposes of diagnosis, administration of medical treatment, or surgery.

It is a further object of the invention to provide system and method for intravenous insertion or extraction of fluids under adverse lighting conditions or in lighting conditions normally found in hospital environments (such as wards, emergency, operating, and recovery rooms) for magnified or non-magnified visualization.

It is a further object of the invention to provide system and method for insertion or extraction of fluids in an emergency situation or to patients/victims who are difficult to catheterize or phlebotomize.

It is a further object of the invention to provide system and method for insertion or extraction of fluids in a hospital environment (such as removal of lymphatic fluid/blood from internal injury).

It is another object of the invention to provide system and method for visualization and identification of foreign bodies and medical appliances in the body.

It is another object of the invention to provide system and method for visualization and identification of veins, arteries and other subcutaneous structures in classes of patients in which the vascular system is difficult to visualize (such as pediatric, geriatric, obese, burn, etc).

It is yet another object of the invention to provide system and method for visualization and identification of veins, arteries and other subcutaneous structures in animal subjects.

It is yet another object of the invention to provide system and method for visualization of underlying tissue exposed during surgical procedure and imaging tissue which is tagged or decorated with an absorbing dye.

These and other objects of the invention will be more fully appreciated by one skilled in the applicable art as a detailed description of representative embodiments thereof proceeds.

BRIEF DESCRIPTION OF THE DRAWINGS

The invention will be more clearly understood from the following detailed description of representative embodiments thereof read in conjunction with the accompanying drawings wherein.

DESCRIPTION OF THE BEST MODE FOR CARRYING OUT THE INVENTION

Description of the Invention

Figure 1:
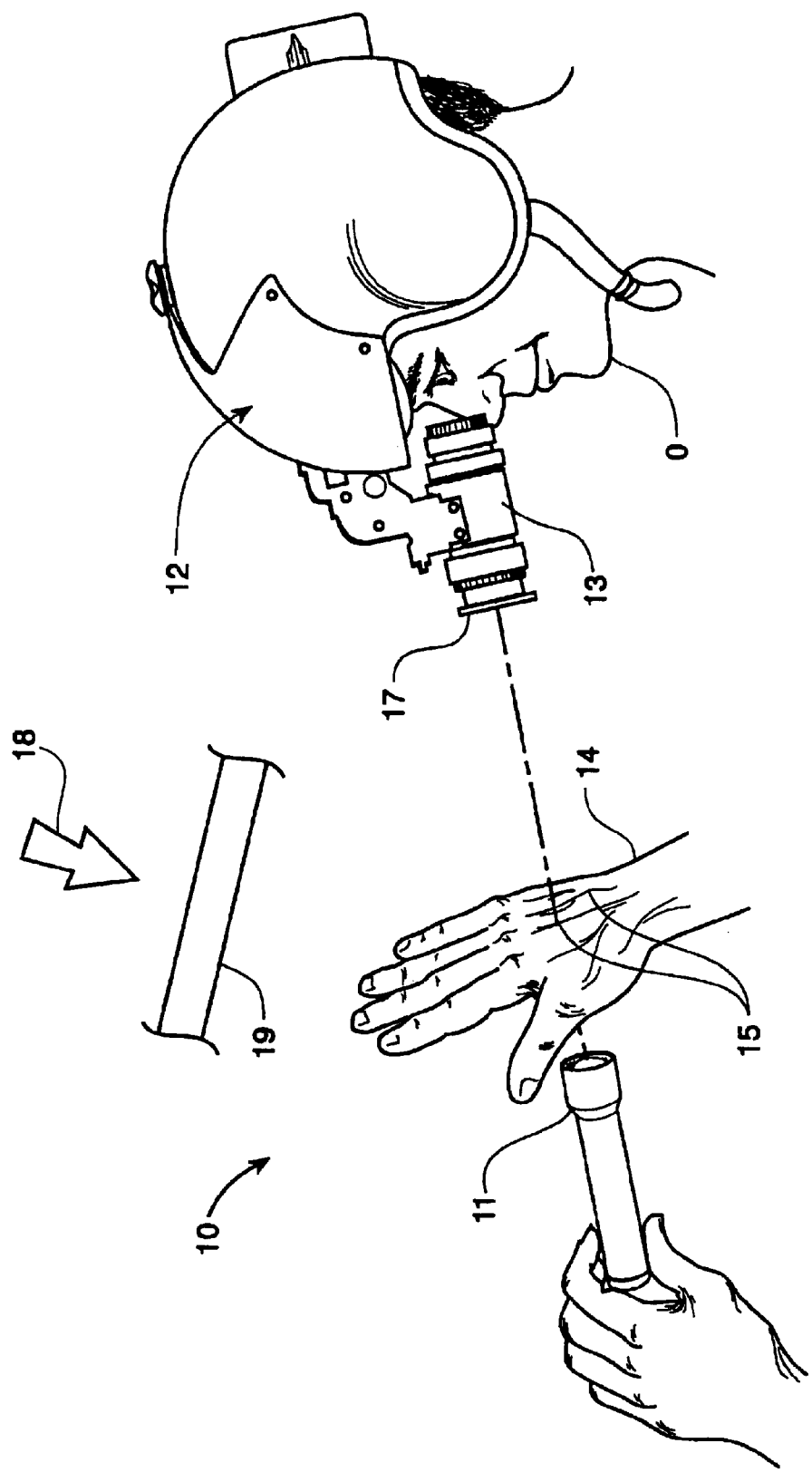
FIG. 1 illustrates a representative embodiment of the invention for the visualization of subcutaneous structures of the human body, such as the hand and forearm shown.

In accordance with a governing principle of the invention, subcutaneous structures, such as vein or artery structures in soft tissue of the body or cysts, cancers, tumors, foreign bodies, medical appliances, or other abnormal structures may be visualized by illuminating or transilluminating the corresponding body portion with light of appropriate spectral composition located in the UV through NIR from a source such as an LED, laser, chemiluminescent, incandescent or fluorescent source (see *IES Lighting Handbook*, J. E. Kaufman, Ed., Illuminating Engineering Society of North America, New York (1984)), and viewing through an image intensifier tube such as that included with a commercially available night vision device (referred to herein generically as NVGs), or other suitable low level light detection means as would occur to the skilled artisan guided by these teachings, including those described briefly hereinbelow. FIG. 1 illustrates a representative system 10 of the invention usable by observer O in viewing subcutaneous structures of the human body 14 (represented by the hand and forearm shown) utilizing a low-level light detection means represented by a commercial NVG 12. System 10 may therefore include light source 11 of selected wavelength(s) in the UV, visible, or NIR, depending on the type of image intensifier means (tube 13) used and on the particular subcutaneous structure of interest. Body portion 14 containing the structure to be visualized may be illuminated directly (in a reflection mode), or, preferably and where the thickness (and consequent degree of absorption and/or scatter) of the tissue of body portion 14 permits, by transillumination through body portion 14. In the practice of the method of the invention, source 11 may be placed near body portion 14 to illuminate the surface thereof in the reflection mode of operation. Alternatively (and preferably), light source 11 is placed near or against the surface of body portion 14 opposite the surface to be viewed so that light from source 11 is transmitted through body portion 14. As shown in FIG. 1 the light source is placed on the palm side of the hand and the viewer is placed on the back side in order to view the veins of the hand that are most desirable for access by a phlebotomist. The orientation or illumination direction is chosen depending on the subcutaneous structure that is to be viewed. Because of the differences in absorption characteristics among venous blood, arterial blood, and any abnormal structures as compared to the skin, bone and surrounding muscle and fatty tissue, the visualization of the location and arrangement of the veins 15, arteries or other structures may be visualized using image intensifier tube 13 of appropriate spectral sensitivity. Filter 17 may be used in conjunction with tube 13 to narrow the spectral range of viewing or to exclude light noise which might interfere with the visualization of the specific subcutaneous structure of interest. For example, an optical filter of the interference structure type (such as fabricated using rugate or stack technology, yielding filter types such as bandpass (cavity, Fabry-Perot, induced transmission) low pass, high pass, band stop, or tunable filters which may be found by reference to W. E. Johnson et al, "Introduction to Rugate Filter Technology, Inhomogeneous and Quasi-Inhomogeneous Optical Coatings," *Proc SPIE* 2046, 88–108 (1993); or to H. A. Macleod, *Thin Film Optical Filters,* 2nd Ed, Macmillan, New York (1986)), or an absorbing structure (which may be found by reference to Schott Glass Technologies, Inc., *Optical Glass Filters*, Dureya, Pa. (1986) and *Infrared Dyes*, M. Matsuoka, Ed., Plenum Press, New York (1990)), or a combination of the two, may be used to select the spectral range of viewing into narrow transmission band(s) to allow use of system 10 in daylight, to differentiate venous from arterial blood or to exclude noise or other radiation not contributing to the desired image. It is noted that filtering competing light sources in the passband(s) of interest improves the contrast ratio or signal-to-noise ratio for system 10. The absorbing structure can be the substrate (such as glass or plastic) and/or optical coating while the interference structure is typically the coating. The specific filter for accomplishing a particular spectral sensitivity may be selected by one skilled in the applicable art guided by these teachings, the same not considered limiting of the invention herein. Ambient light 18 may be excluded from the spectral range of interest by performing the method of the invention in an environment suitably shielded by filter means represented in FIG. 1 by filter 19.

Image Creation

In the contemplation of the invention, the image of the scene can be visualized utilizing various low-level light detection means. In a first such mean, viz., a staring system, a lens is placed in front of a detector array such as a CCD or the photocathode of an image intensifier tube, such as is commonly used in commercially available night vision goggles. A second such means comprises sequential radiance measurement of the scene using a single detector element, such as a photomultiplier tube or photodiode, which serially scans the entire field of view in some fashion (raster, circular, helical, etc). The position of each element of the scene is registered with the position of the image on the output display such as a television monitor. A third means comprises use of a linear detector array to scan the image of the scene across the detector along a line of azimuth or elevation, such as in an optical system in an infrared reconnaissance system.

Low-Level Light Imaging Tube Technology

A prominent technology for the detection and amplification of a scene under low light conditions is based on vacuum tubes. An image intensifier tube is sensitive down to starlight levels (typically 0.0001 foot-candles, 0.0010764 lumen/meter$^2$), whereas the typical solid state array based camera needs about 1 foot-candle (10.764 lumen/meter$^2$). Through the selection of an appropriate photocathode material, tubes can process radiation from the UV through the visible to the NIR.

The low light level performance of a camera system may be enhanced by coupling an electrostatically focused intensifier tube to a standard vidicon tube. For increased low light level capability the phosphor screen is replaced with a silicon anode containing p-n junction diodes. When accelerated electrons strike, they create electron hole pairs that are read at the camera's output as an amplified signal. Such silicon intensified target (SIT) tube cameras can construct an image from just 0.001 foot-candles (0.010764 lumen/meter$^2$) illumination. The SIT can be enhanced by adding an intensifier tube to a SIT camera and making an intensified silicon intensified target (ISIT) camera, which can create an image from 0.0001 foot-candles. The dynamic resolution of the SIT may be improved by combining an intensifier with a charge coupled device (CCD) to create an intensified charge coupled device (ICCD).

Video intensified microscopy has been developed for low light level imaging, comprising a two element detector including a two dimensional photon counting tube optically coupled to a high performance low lag vidicon. The photon counting tube consists of a photocathode and a two stage microchannel plate (MCP) and a phosphor screen, which system has a wide dynamic range from photon counting to ordinary low light level imaging.

Image Intensifier Tubes

A description of the structure and operation of various types of image intensifier tubes useful in the system of the invention or in the practice of the method thereof may be found by reference to Illes. P. Csorba, *Image Tubes* (Howard W. Sams & Co. Inc, Indianapolis, 1985). Accordingly, the types of image intensifier tubes which may be included in the structure of the invention represented by system 10 may include a third generation NVG (GEN-III) (for operation at about 0.3 to 0.9 $\mu$m), a second generation NVG (GEN-II) (for operation at about 0.3 to 0.9 $\mu$m), or InGaAs (for operation at about 0.3 to 1.0 $\mu$m), or other type occurring to the skilled artisan guided by these teachings.

Figure 2:
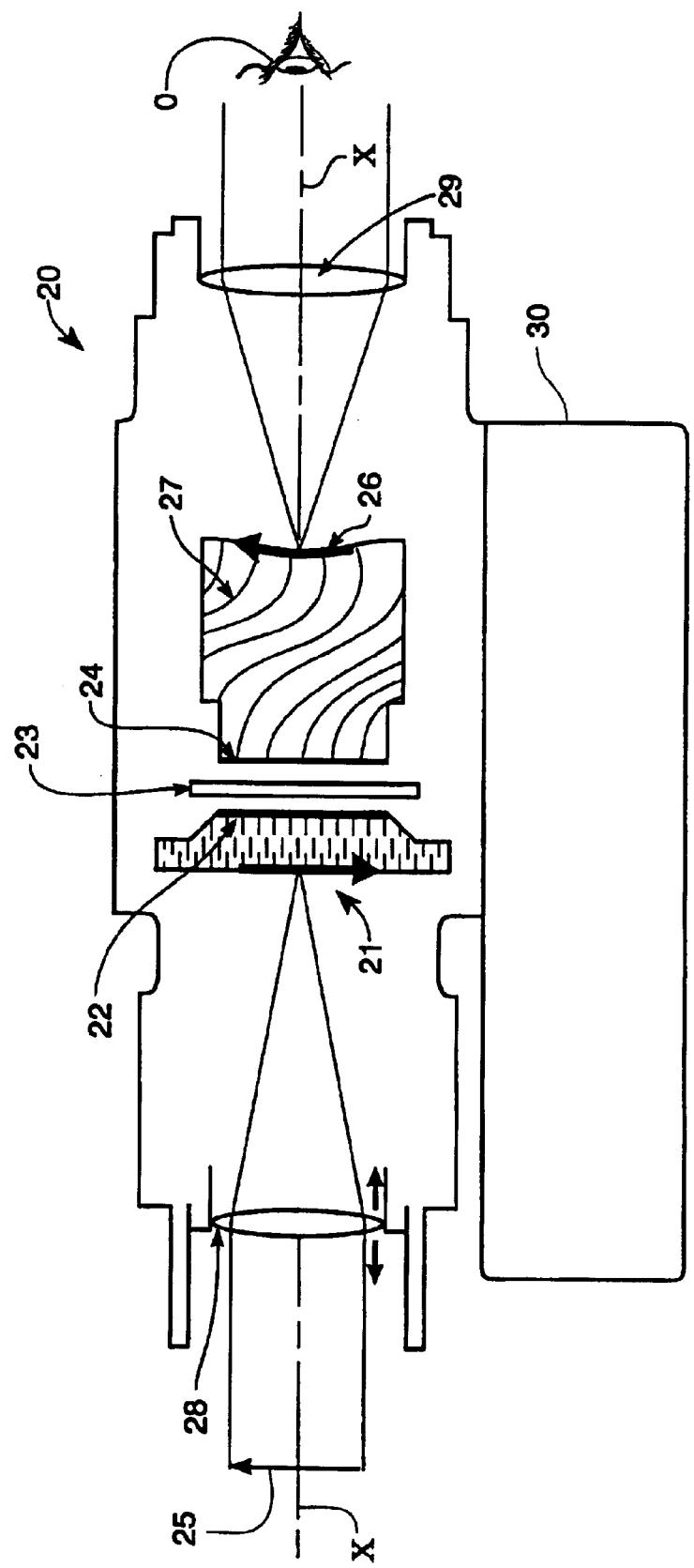
FIG. 2 is a view in axial section of the components of an image intensifier tube included in a commercially available NVG usable as a component of the invention.

The operation of an image intensifier tube may be generally described as electronically amplifying an image illuminated by a low level of lighting, such as that which characterizes nighttime light, or illuminated by light in regions of the electromagnetic spectrum to which the human eye is not sensitive, viz., the NIR and UV regions of the spectrum. Accordingly, and with reference now to FIG. 2, shown therein is a view in axial section of a representative image intensifier tube used in the structure of commercially available NVGs and having the general structure useful as a component of the invention. (General discussions of the structure and operation of NVGs may be found by reference to Thomas J. Tredici et al, *Night Vision Manual for the Flight Surgeon*, USAFSAM-TR-85-3 (1985), or to F. Baratte et al, "Night Vision Tubes and Solid-State Devices," *Special Electronics* (1984), 36–41). Intensifier tube 21 of NVG 20 is a high vacuum tube comprising three basic components, viz., photocathode 22 disposed on a fiberoptic faceplate, microchannel plate (MCP) 23 and phosphor screen 24 disposed axially along viewing axis X. Photocathode 22 converts photons of light from low-level light image 25 into electrons. MCP 23 comprises a multiplicity of coaxially disposed optical channels in which the electrons from photocathode 22 are amplified. Phosphor screen 24 converts the electrons from MCP 23 into a visible image 26 for display to and viewing by observer O. NVG 20 otherwise may include a fiber optic twist 27 supporting phosphor screen 24 for inverting visible image 26, a focusable objective lens 28, an eyepiece lens 29 for magnifying image 26 for viewing by observer O, and an associated battery pack 30 for providing power to photocathode 22 and MCP 23 and portability to NVG 20. A single tube 21 may be included in a monocular NVG or two tubes may be included in a binocular system.

Figure 3:
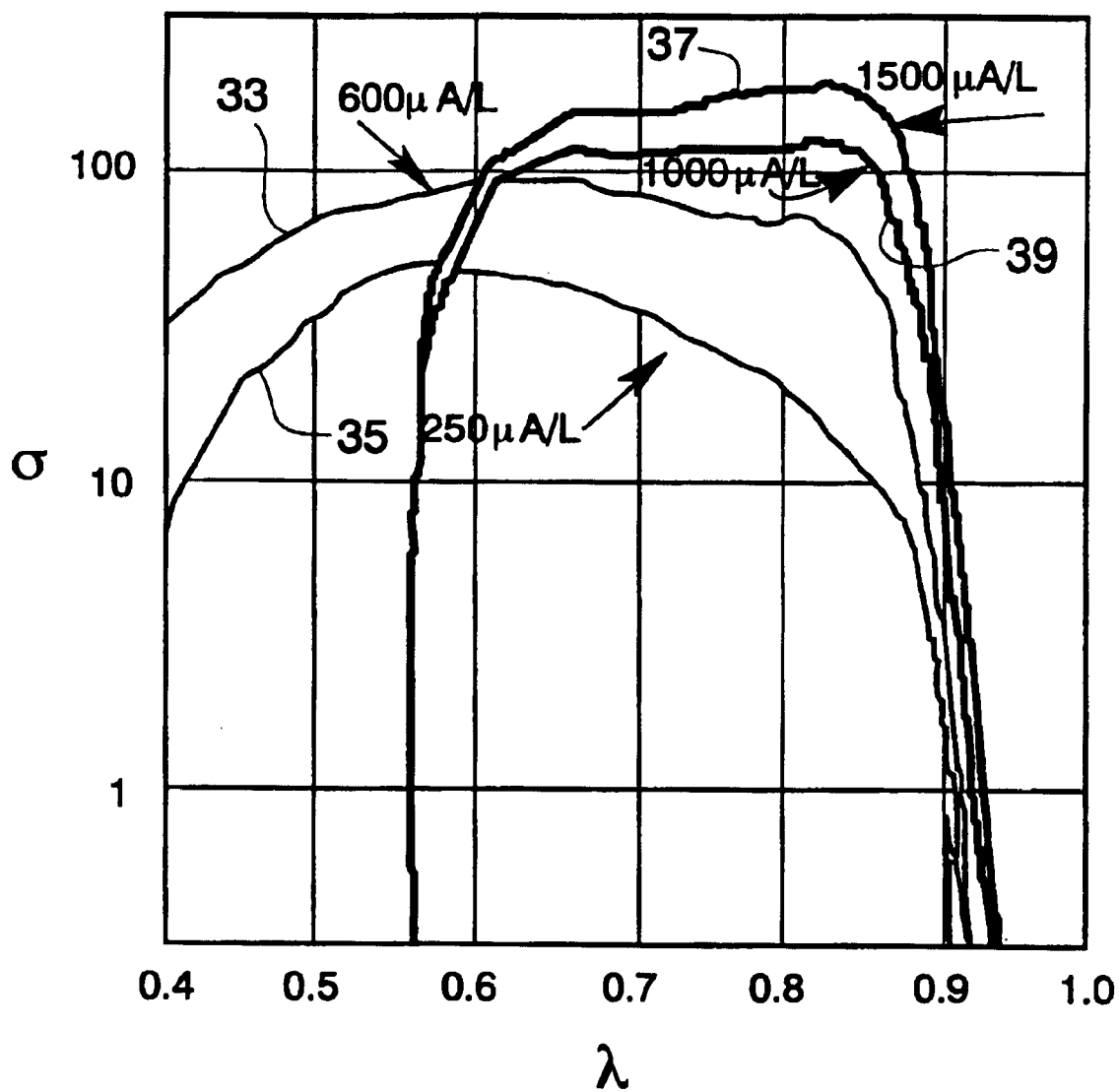
FIG. 3 is a graph of absolute sensitivity versus wavelength which shows spectral responses of generation II and III NVGs.

Referring now to FIG. 3, shown therein are plots of absolute sensitivity $\sigma$ (mA/W) versus wavelength $\lambda$ (in microns) defining the spectral response of Generation II and aviator Generation III NVGs. FIG. 3 suggests that the GEN-II NVG (defined by plots 33 and 35) is sensitive to the spectral range of about 0.4 to 0.9 μm, whereas the aviator GEN-III NVG (defined by plots 37 and 39) is sensitive to the range of about 0.6 to 0.9 μm. However, enhancements to GEN-III NVGs have extended the spectral range of operation down to about 0.3 μm and up to about 1.0 μm. The primary difference between the second and third generation image intensifier tubes embodied, respectively, in the GEN-II and GEN-III NVGs, are that the GEN-II tubes typically include tri-alikali photocathodes sensitive to the visible portion of the spectrum, whereas the GEN-III tubes typically include gallium arsenide photocathodes sensitive to the NIR (up to about 0.94 μm) portion of the spectrum. An NVG permits the user to see in the visible through the NIR and enhance the vision capabilities of the user by increasing the illumination levels by about a factor of about $10^4$ to $10^5$. It is noted that other image intensifier tube types may be selected for use, within the scope of these teachings and the appended claims, as would occur to the skilled artisan practicing the invention, depending on the desired spectral sensitivity of the system and in consideration of the subcutaneous structure of interest.

Charge-Coupled Devices

The image sensing capability of the CCD is based on the absorption of incident radiation in the silicon which generates a linearly proportional number of free electrons in the specific area of illumination. The CCD array is composed of a repetitive pattern of small photosensing sites, each generating a charge packet in direct response to the incident radiation. By creating an image of the external scene on the array, the charge packet distribution in the array will reproduce the light distribution in the scene. At regular intervals, the charge packets along one column of the array are simultaneously transferred by charge coupling to a parallel CCD analog transport shift register. The photosites are then returned to a new iteration of image collection. While the photosites are collecting a new image, the CCD analog transport register is rapidly clocked to deliver the picture information in serial format to the device output circuitry. The output circuit delivers a sequence of electrical signals in which the amplitude is proportional to the amount of charge generated at each photosite. By mapping the signal back to the individual photosites, it is possible to recreate the scene image.

Photomultiplier Tubes and Photodiodes

Photomultiplier tubes utilize photoemission and secondary-electron emission in order to detect very low light levels. (See e.g., *Photomultiplier Tubes*, Hamamatsu Photonics K.K. (December 1986)). Typical applications of these devices include photographic instruments, optical pattern recognition, x-ray and nuclear medical instruments, star and planet tracking for guidance systems, and analytical instruments. The photomultiplier tube is a photosensitive device consisting of a photoemissive cathode followed by focusing electrodes, an electron multiplier and an electron collector, i.e. the anode in a vacuum tube. When light enters the photocathode, the photocathode emits photoelectrons into the vacuum which are accelerated and focused onto a secondary-emission surface, the dynode, from which several electrons are emitted for each incident primary electron. The secondary electrons are then directed onto a second dynode where more electrons are released. This process is repeated a number of times depending upon the number of dynodes used. The multiplied electrons are then collected by the anode as an output signal. In this manner it is possible to amplify the initial photocurrent by a factor of $10^8$ or more.

Many different types of photcathodes are used in photomultipliers. Typical materials and combinations used include cesium-oxygen-silver (Cs—O—Ag) which is sensitive to radiation from the visible to the NIR. Cesium-antimony (Cs—Sb) has a spectral response from the UV through the visible spectrum. Bialkali (Sb—Rb—Cs, Sb—K—Cs) materials have an enhanced spectral response from the UV through visible spectrum. Multialkali (Na—K—Sb—Cs) photocathode materials have a wide spectral response from the UV to the NIR. Gallium arsenide photocathodes activated with cesium (GaAs(Cs)) have a wider range from the UV to the NIR than typically characterizes the multialkali materials.

Photodiodes are generally useful for low light detection and operate in the range of about 200 to 1105 nanometers (nm). The diode junction acts as a photodetector. An electron hole pair can be created by an incident photon provided that the photon energy is greater than the semiconductor band gap energy. This can occur in any of the semiconductor layers. Once carriers are created, a current will flow until they are collected or recombined. Two basic types of photodiodes are typically used: silicon PIN photodiodes and the silicon avalanche photodiodes (APD). At low frequencies and at low but not ultralow signal levels, a PIN photodiode is preferred. At lower light levels, avalanche photodiodes are preferred. A high reverse bias voltage leads to a high field in the p-n junction region. Photogenerated or thermally generated carriers that reach this region are accelerated to energies at which collisional ionization occurs resulting in a multiplication of carriers thus resulting in internal gain. APDs can have quantum efficiencies in excess of 90% and noise equivalent powers less than $10^{-15}$ W/Hz$^{-1/2}$.

The Light Source

Figure 4:
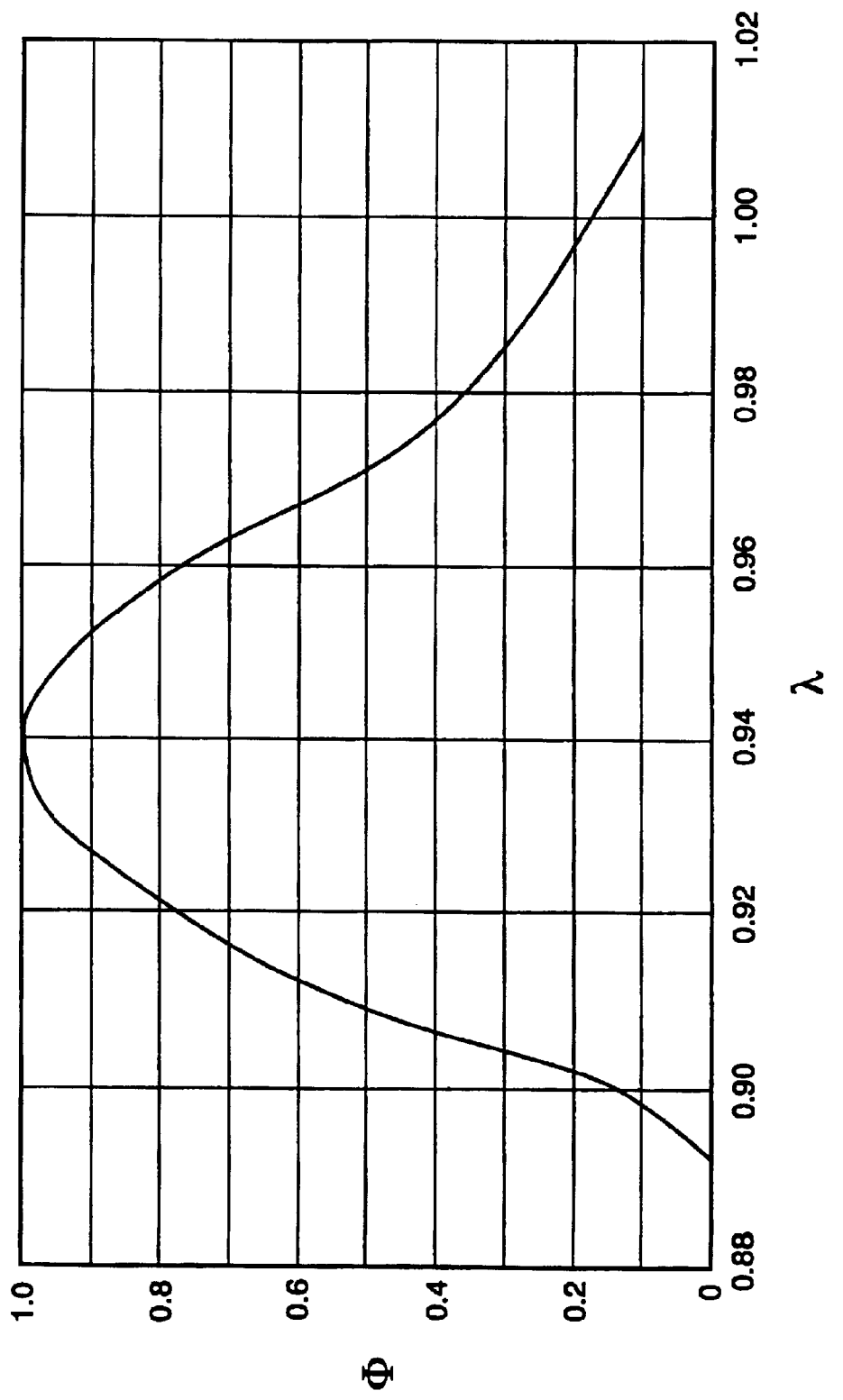
FIG. 4 is a graph of relative output power versus wavelength which shows the spectral emission characteristics of a typical commercially available NIR light emitting diode (LED)
Figure 5:
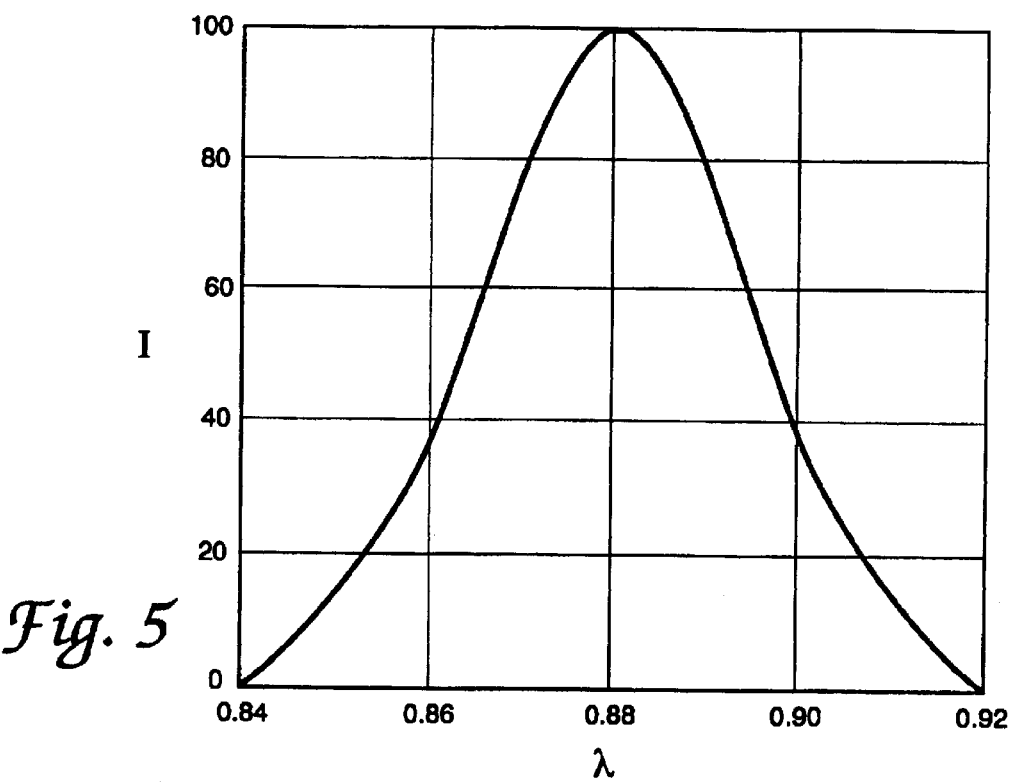
FIG. 5 is a graph of relative emission intensity versus wavelength which shows the spectral emission characteristics of an NIR LED preferred for use as a source in an embodiment of the invention.
Figure 6:
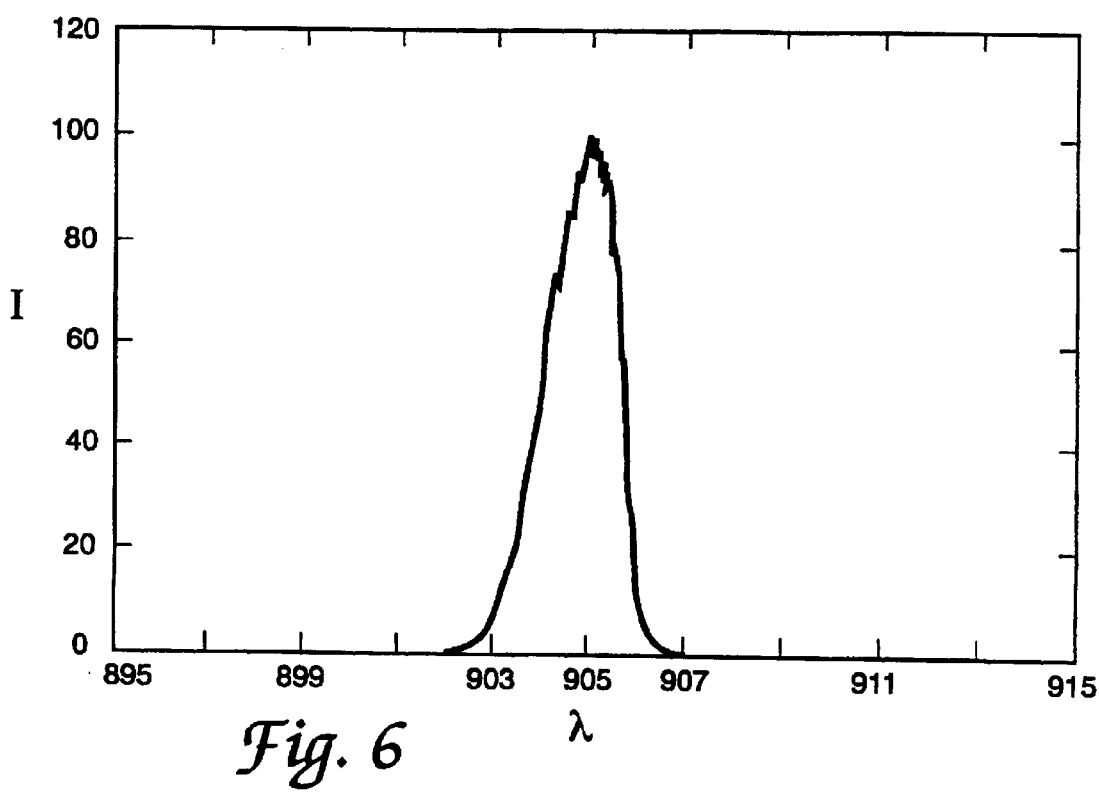
FIG. 6 is a graph of relative emission intensity versus wavelength which shows the spectral emission characteristics of an typical commercially available NIR laser emitting diode.

Selection of the light source (FIG. 1, #11) for illuminating (in the reflection mode) or transilluminating the body portion (FIG. 1, #14) of interest may also be made by the skilled artisan practicing the invention in consideration of the intended use of the system (such as 10 in FIG. 1) in visualizing a particular subcutaneous structure, such as for facilitating the location of a vein for insertion of an intravenous needle for blood transfusion or administration of an injection or other medication. Observations made in demonstration of the invention in the reflection mode for an NIR light source showed that sufficient contrast to show veins in the hand and forearm could be achieved over the 0.6 to 0.9 μm band using a GEN-III NVG; above about 0.94 μm the NVG response falls off (FIG. 3). Similar demonstration experiments proved the utility of the invention to allow visualization of an abnormal occlusion in a female breast. It is noted that light in substantially any region of the spectrum, including UV, visible or infrared (IR), may be used as a source. However, an IR source is preferred because of the lesser scattering associated with an IR source than with sources of shorter wavelength, IR exhibits better transmission characteristics through body tissue, image intensifier tubes (particularly NVGs) operate more efficiently in the IR, filters are easier to make for the IR, and there is less extraneous ambient IR light to contend with in the practice of the invention. For example, FIG. 4 is a graph of relative output power Φ versus wavelength λ (microns) which shows the spectral emission characteristics of a typical commercially available LED (such as Mitsubishi model CD-2060-R) used in an IR remote control device, having a spectral peak centered at about 0.94 μm. FIG. 5 is a graph or relative emission intensity I (percent) versus wavelength λ (microns) which shows the spectral emission characteristics of a narrow band commercially available LED (Hitachi model HE 8801 GaAlAs IRED) which may be preferred for use with the invention because of its characteristic spectral peak at about 0.88 μm. A laser provides an even narrower band source of light. FIG. 6 is a graph of relative emission intensity I versus wavelength λ (nanometers) which shows the spectral emission of a GaAs light emitting diode laser source having a peak output wavelength at 905 nanometers and a bandwidth of only a few nanometers. The light emitting diode laser is a solid state device employing a p-n junction in a semiconducting crystal. A narrow spectral emission band is produced by the recombination of electrons and holes in the vicinity of the junction when a small bias voltage is applied in the forward direction. The peak output wavelengths for light emitting diode lasers are found over visible and near infrared wavelengths (from *The Laser Focus World Buyers Guide* '96, Vol 31, A PennWell Publication (December 1995)). The spectral location of the peak output wavelength is determined by selecting one of a variety of alloy semiconductor materials such as GaAs, InGaAs or SiC, and by varying the composition of the selected semiconductor. Note that the peaks of FIGS. 4, 5 and 6 lie within the spectral sensitivity range of the GEN-II and GEN-III NVGs as suggested in FIG. 3. While the utility of the invention has been demonstrated using a variety of sources, further source enhancements can be made by one skilled in the art guided by these teachings.

Figure 7:
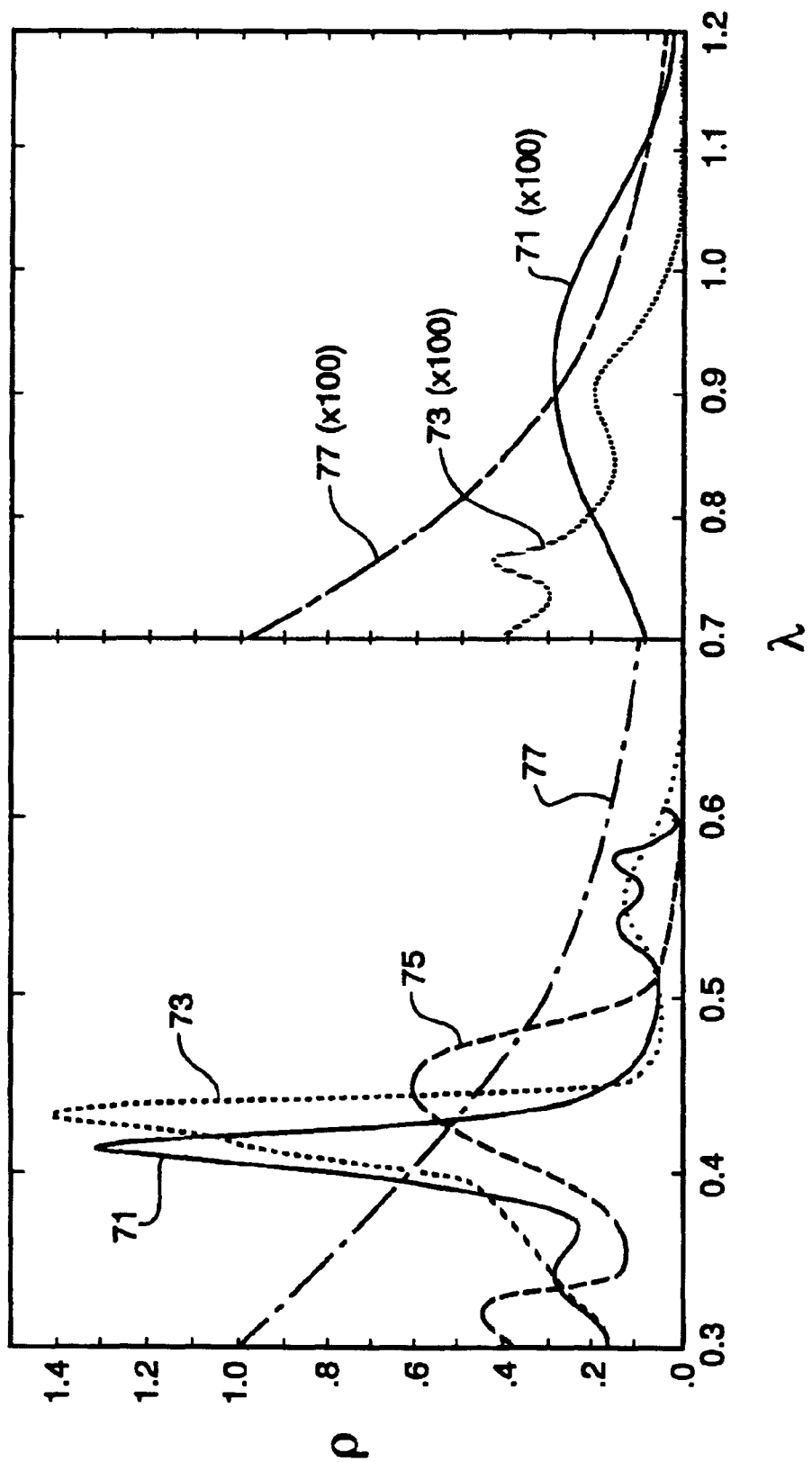
FIG. 7 is a graph of molar extinction coefficient versus wavelength which shows the absorption spectra of selected components of human blood.
Figure 8:
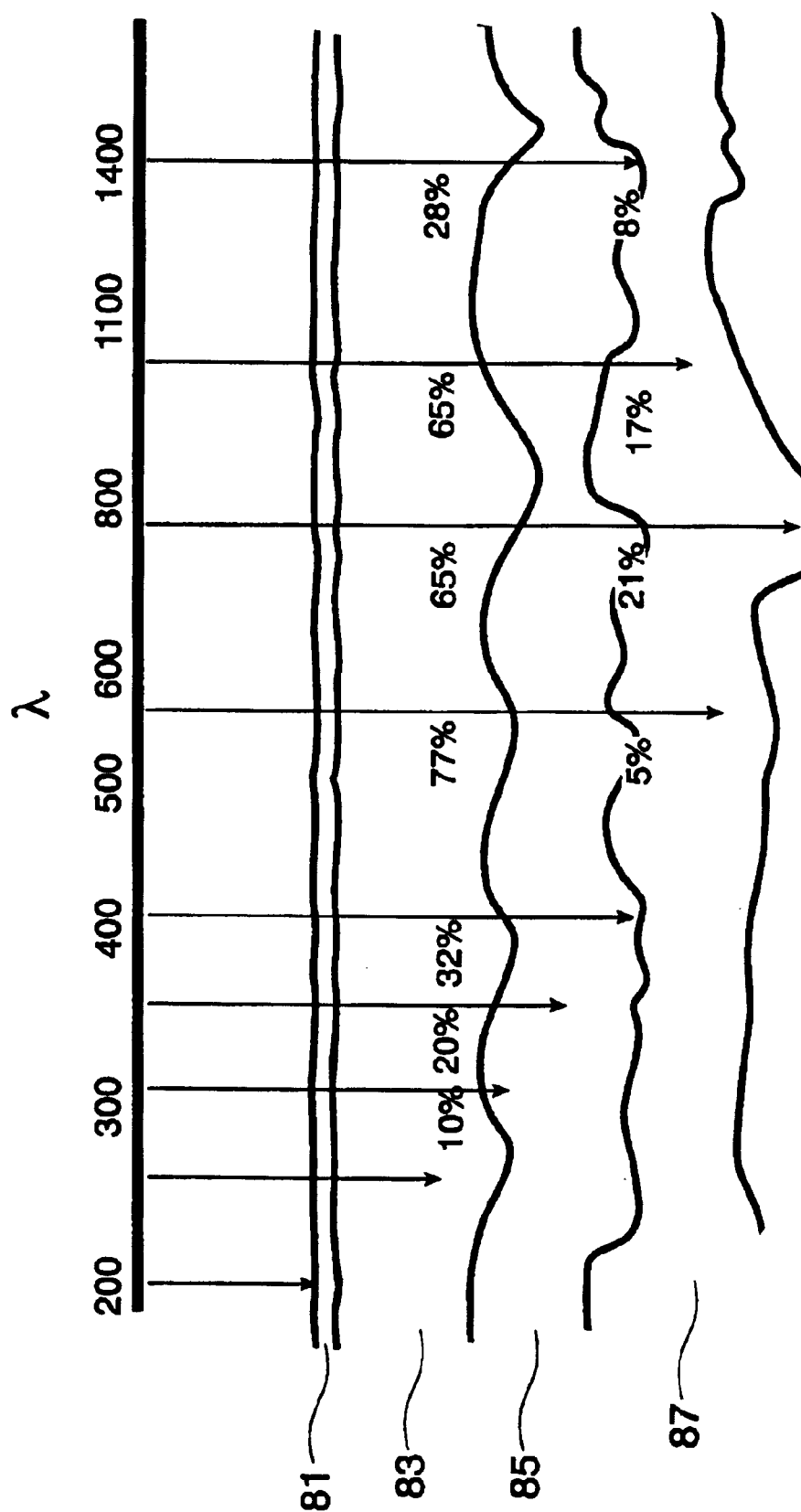
FIG. 8 shows a schematic of the percent human skin depth penetration of various wavelengths of light.
Figure 9:
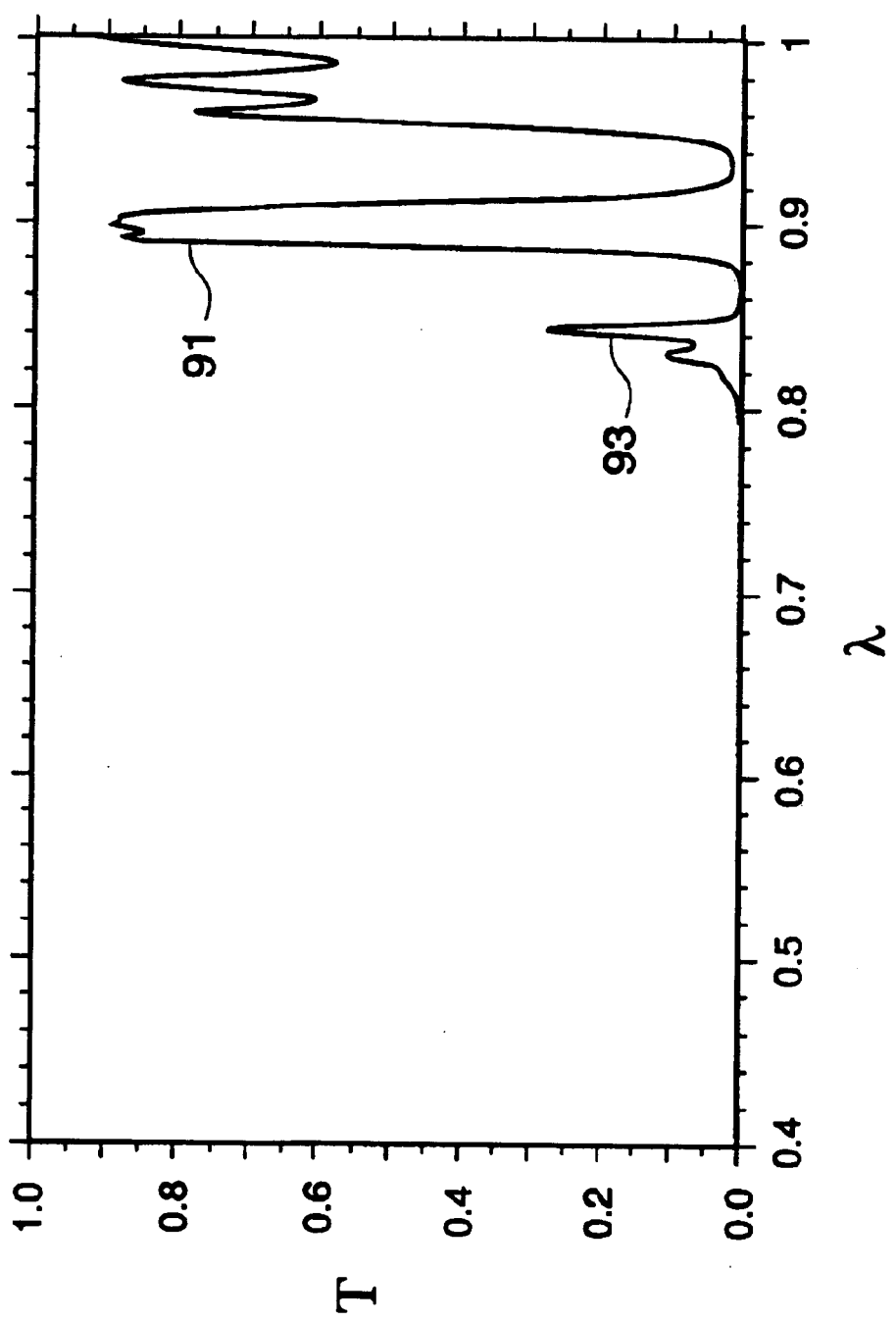
FIG. 9 is a graph of transmittance versus wavelength defining the transmittance spectra of a fabricated combination absorber and rugate filter structure.
Figure 10:
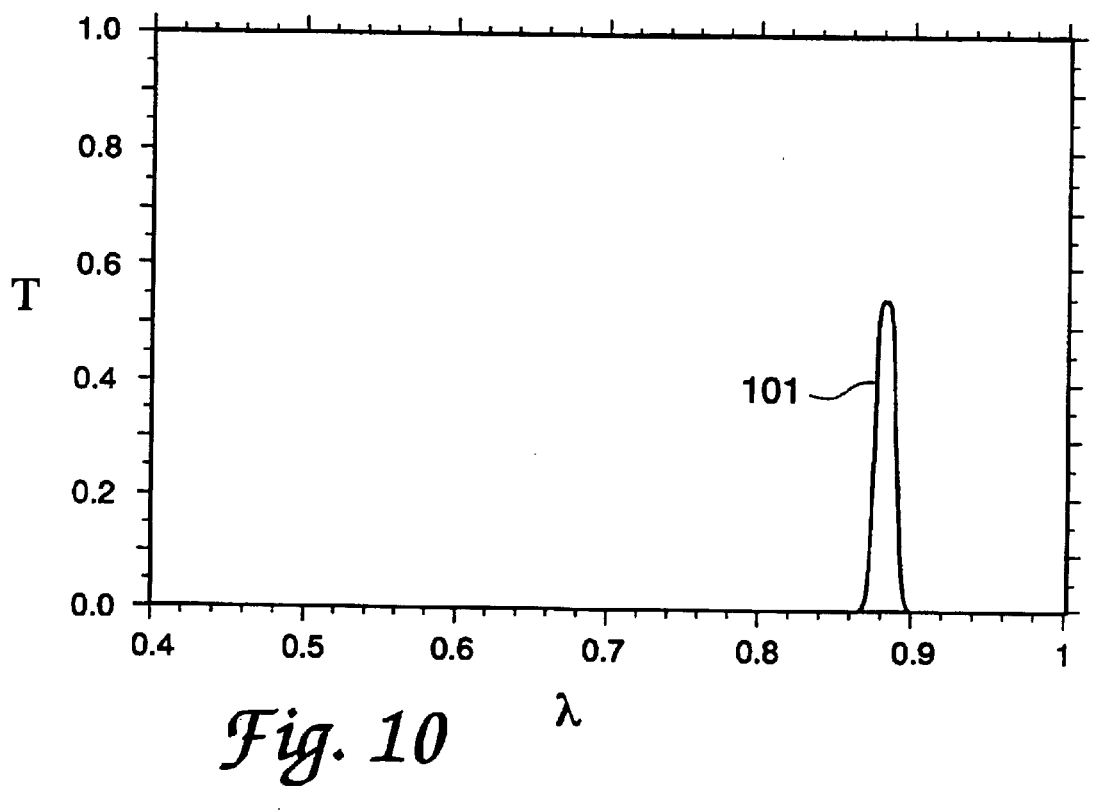
FIG. 10 is a graph of transmittance versus wavelength defining the transmittance spectra of a commercially fabricated combination absorber and dielectric stack filter structure.

Human skin readily transmits IR and the underlying or subcutaneous structures attenuate IR generally by scattering in the case of muscle fiber or by absorption in the case of oxygenated and deoxygenated hemoglobin. Referring now to FIG. 7, shown therein is a plot of molar extinction coefficient ρ (lumen/mole/cm) versus wavelength λ (microns) defining the absorption spectra of selected components of human blood (from R. R. Anderson et al, "The Optics of the Human Skin," *The Journal of Investigative Dermatology*, 77 (1), 13–19 (1981)). In FIG. 7, solid line 71 represents oxygenated hemoglobin and exhibits sharp peaks in the visible spectrum at about 0.345, 0.41, 0.54 and 0.58 μm and a broad peak in the NIR centered at about 0.92 μm. Dotted line 73 represents deoxygenated hemoglobin and exhibits a sharp peaks in the visible at about 0.43 μm, a broad peak in the visible centered at about 0.56 μm and peaks in the NIR at about 0.7, 0.76 and 0.9 μm. Dashed line 75 represents bilirubin and exhibits peaks in the visible at about 0.32 and 0.455 μm. Broken line 77 represents DOPA-melanin and exhibits no remarkable spectrum in the wavelength ranges of interest. FIG. 8 shows a diagram of percent human skin depth penetration of various wavelength λ (microns) of light from the UV through the NIR (from D. Sliney et al, *Safety With Lasers and Other Optical Sources: A Comprehensive Handbook*, Plenum Press, New York (1985)) showing that for the wavelengths of greatest interest in the practice of the invention, penetration of light into the skin and soft tissue of the body is substantial. In FIG. 8, layers 81, 83, 85, and 87 respectively represent the stratum corneum, stratum malpighl, derma, and subcutis. The venous structure was viewed by an NVG in a darken room. FIG. 9 is a graph of transmittance T versus wavelength λ (microns) which shows the transmittance of a fabricated combination absorber and rugate structure (Schott glass RG-850 coated with a two reflection band rugate filter (from W. E. Johnson et al, "Introduction to Rugate Filter Technology, Inhomogeneous and Quasi-Inhomogeneous Optical Coatings," *Proc SPIE* 2046, 88–103 (1993)) having a narrow passband 91 of 0.023 μm FWHM which is centered at 0.898 μm. The Schott glass highly absorbs light having wavelengths below about 0.8 μm while the rugate coating reflects light on either side of the passband. The passband transmits about 87% of light located near the center wavelength of 0.898 μm. For this particular filter, a small amount of noise 93 is transmitted from about 0.81 μm to about 0.85 μm. FIG. 10 is a graph of transmittance T versus wavelength λ (microns) shows the transmittance of a fabricated combination absorber and stack coating structure. This filter has a narrow passband 101 of 0.015 μm FWHM which is centered at 0.882 μm. This filter, as does the filter of FIG. 9, absorbs and/or reflects wavelengths which are not within the desired passband. Passband 101 for the FIG. 10 filter peaks to about 55% at the center wavelength. Both filter types of FIG. 9 and FIG. 10 have been used in observations made in demonstrating the invention with LED sources emitting light centered around 0.88 μm. In consideration of the data presented in FIG. 7, FIG. 8, FIG. 9 or FIG. 10, and as an example of the utility of the invention, filters of the combination absorber (in the substrate as dyed glass, dyed plastic, undoped gallium arsenide, doped gallium arsenide, etc or in the coatings) and rugate/stack (blended or non-blended materials to achieve a prescribed refractive index coating) structure having a narrow passband(s) at, for example, 0.41, 0.43, 0.76 or 0.89 μm may be used in conjunction with a commercially available image intensifier tube (e.g., a GEN-III NVG) to differentiate venous blood from arterial blood from surrounding tissue. However, observations made in demonstration of the invention showed good venous structure in hands transilluminated by a Ti-sapphire laser tuned from 0.708 to 0.870 microns with an output power ranging from 6 to 25 milliwatts.

Figure 11:
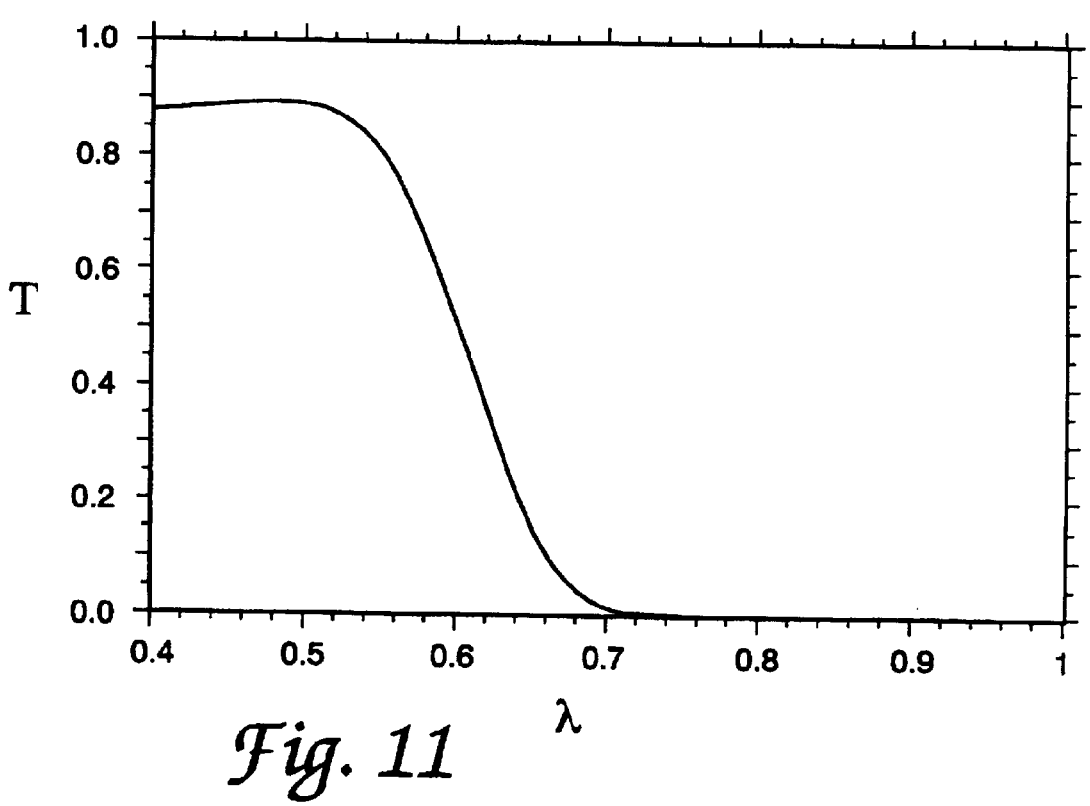
FIG. 11 is a graph of transmittance versus wavelength defining the transmittance spectra of a commercially available NIR absorbing glass.
Figure 12:
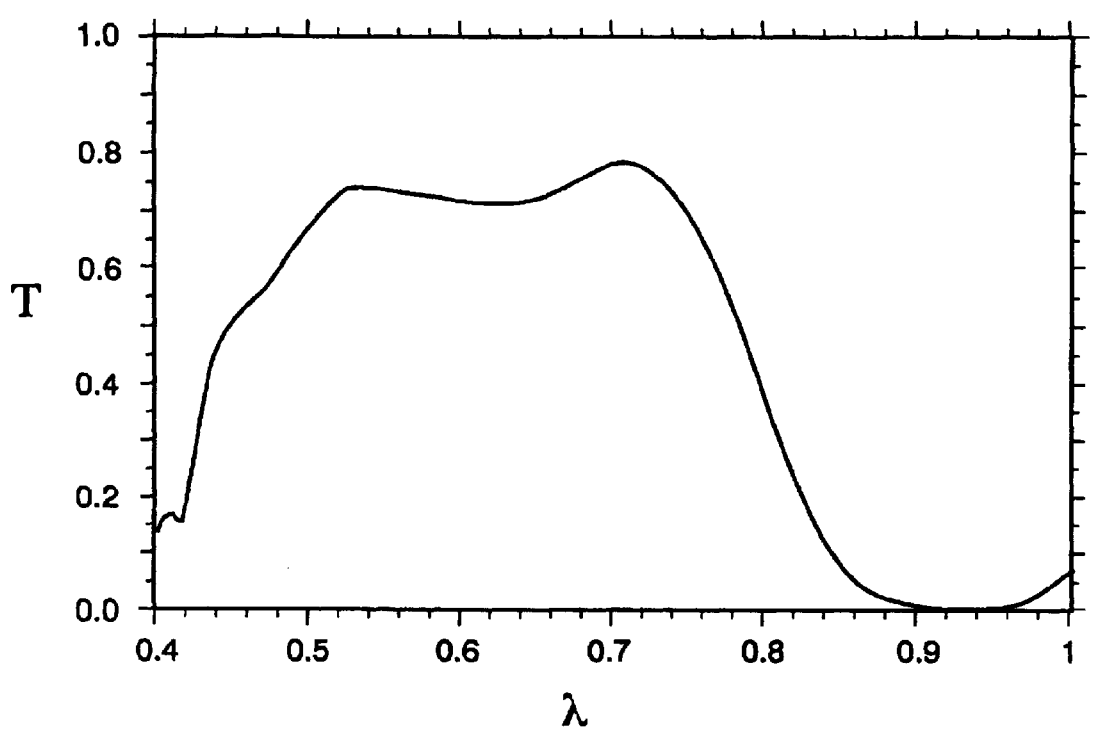
FIG. 12 is a graph of transmittance versus wavelength defining the transmittance spectra of an NIR absorbing dye in a plastic host.

The contrast ratio or signal-to-noise-ratio (SNR) drives the spectral performance of both source and filter. For example, using a narrow band light source, such as a laser emitting diode, and a filter having passband(s) which are very narrow (a few nanometers FWHM) and highly transmitting (>80%) will yield a good SNR. Filters having high attenuation (about $10^{-4}$ to $10^{-5}$) outside of the passband(s) will further improve the SNR. Increasing the illuminance of the background lighting; such as found in a windowless but, highly lit operating room at a hospital, decreases the SNR. However, lighting covers which transmit visible wavelengths (>80%) but, highly attenuate NIR wavelengths (about $10^{-4}$ to $10^{-5}$) negate this decrease in the SNR. These lighting covers can be either glass, such as Schott BG 39 or BG 40, or a polymer or plastic, e.g., polymethylmethacrylate, impregnated with materials such as nickel dithiolene complexes. FIG. 11 is a graph of transmittance T versus λ (microns) which shows the transmittance of a one-millimeter thick Schott BG 39 glass having broad NIR absorption while FIG. 12 is a graph of T versus λ which shows the transmittance of a nickel dithiolene complex having a much narrower absorption band which is wavelength tunable as the chemical composition is varied. For this case the room would have little NIR, due to the light covers, but, a person would see visible wavelengths transmitted through the light covers. However, the background noise at NIR wavelengths is dramatically reduced which allows seeing subcutaneous structures using an NVG with a NIR light source and filters having the appropriate NIR passband(s).

The entire teachings of all references cited herein are incorporated herein by reference.

INDUSTRIAL APPLICABILITY

The invention therefore provides system and method for enhanced, non-invasive or invasive surgical procedures (e.g., angiography) visualization or identification of subcutaneous structures of the body. In the practice of the invention, the detection, identification and mapping of veins, arteries and other subcutaneous structures in human or animal subjects may be performed under adverse lighting conditions associated with the emergency administration of medical treatment or in lighting conditions which could be found in hospital environments, for purposes of diagnosis, administration of medical treatment, and surgery, or for visualization and identification of foreign bodies and medical appliances in the body.

It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

What is claimed is:

1. A system for enhancing the visualization of veins, arteries and other subcutaneous natural or foreign structures in the body, comprising:
   (a) a light source for illuminating a portion of the body in at least one of a reflection mode and a transillumination mode;
   (b) at least one low level light detection means for detecting low light levels having spectral characteristics defined by the relative light absorption properties of subcutaneous structures within said portion of the body, said low light levels reflected from or transmitted through said portion of the body, and for generating an image of subcutaneous structures within said portion of the body, and means for displaying said image; and
   (c) wherein said at least one low level light detection means includes a device selected from the group consisting of an image intensifier tube, a photomultiplier tube, a photodiode and a charge coupled device.

2. The system of claim 1 wherein said image intensifier tube is a night vision device.

3. The system of claim 1 wherein said light source includes wavelengths in a wavelength range defined from about 0.3 to about 1.0 micron and said at least one low level light detection means is sensitive to selected wavelength bands within said wavelength range.

4. The system of claim 1 wherein said at least one low level light detection means is one of a monocular arrangement providing independent viewing of two spectral visual fields of said image and a binocular arrangement providing depth perception of said image.

5. A system for enhancing the visualization of veins, arteries and other subcutaneous natural or foreign structures in the body, comprising:
   (a) a light source for illuminating a portion of the body in at least one of a reflection mode and a transillumination mode;
   (b) at least one low level light detection means for detecting low light levels having spectral characteristics defined by the relative light absorption properties of subcutaneous structures within said portion of the body, said low light levels reflected form or transmitted through said portion of the body, and for generating an image of subcutaneous structures within said portion of the body, and means for displaying said image; and
   (c) an optical filter disposed between said source and said at least one low level light detection means for transmitting light only within preselected narrow wavelength bands.

6. The system of claim 5 wherein said light source includes said preselected narrow wavelength bands and said at least one low level light detection means is sensitive to said preselected narrow wavelength bands.

7. The system of claim 5 wherein said source is a narrow band source selected from the group consisting of a light emitting diode and a laser.

8. The system of claim 5 wherein said optical filter has a narrow passband centered substantially on at least one wavelength selected from the group consisting of 0.41, 0.43, 0.76 and 0.89 micron.

9. The system of claim 5 wherein said source is a broadband source selected from the group selected from an incandescent source, a chemiluminescent source and a fluorescent source.

10. The system of claim 5 wherein said at least one low level light detection means is one of a monocular arrangement providing independent viewing of two spectral visual fields of said image and a binocular arrangement providing depth perception of said image.

11. A system for enhancing the visualization of veins, arteries and other subcutaneous natural or foreign structures in the body, comprising:
   (a) a light source for illuminating a portion of the body in at least one of a reflection mode and a transillumination mode;
   (b) at least one low level light detection means for detecting low light levels having spectral characteristics defined by the relative light absorption properties of subcutaneous structures within said portion of the body, said low light levels reflected from or transmitted through said portion of the body, and for generating an image of subcutaneous structures within said portion of the body, and means for displaying said image; and
   (c) means for filtering ambient light at said light source from said at least one low level light detection means.

12. The system of claim 11 wherein said at least one low level light detection means is one of a monocular arrangement providing independent viewing of two spectral visual fields of said image and a binocular arrangement providing depth perception of said image.

13. A system for enhancing the visualization of veins, arteries or other subcutaneous structures in the body, comprising:
   (a) a light source for illuminating a portion of the body in at least one of a reflection mode and a transillumination mode, said light source including preselected wavelength bands;
   (b) at least one low level light detection means for detecting low light levels having spectral characteristics defined by the relative light absorption properties of subcutaneous structures within said portion of the body, said low light levels reflected from or transmitted through said portion of the body, and for generating an image of subcutaneous structures within said portion of the body, and means for displaying said image;
   (c) an optical filter disposed between said source and said at least one low level light detection means for transmitting light only within said preselected wavelength bands; and
   (d) wherein said optical filter has a narrow passband centered substantially on at least one wavelength selected from the group consisting of 0.41, 0.43, 0.76 and 0.89 micron.

14. A system for enhancing the visualization of veins, arteries or other subcutaneous structures in the body, comprising:
   (a) a light source for illuminating a portion of the body in at least one of a reflection mode and a transillumination mode, said light source including preselected wavelength bands;

(b) at least one low level light detection means for detecting low light levels having spectral characteristics defined by the relative light absorption properties of subcutaneous structures within said portion of the body, said low light levels reflected from or transmitted through said portion of the body, and for generating an image of subcutaneous structures within said portion of the body, and means for displaying said image;

(c) an optical filter disposed between said source and said at least one low level light detection means for transmitting light only within said preselected wavelength bands; and (d) wherein said at least one low level light detection means includes a device selected from the group consisting of an image intensifier tube, a photomultiplier tube, a photodiode and a charge coupled device.

15. The system of claim 14 wherein said image intensifier tube is a night vision device.

16. The system of claim 14 wherein said at least one low level light detection means is one of a monocular arrangement providing independent viewing of two spectral visual fields of said image and a binocular arrangement providing depth perception of said image.

17. A method for enhancing the visualization of veins, arteries or other subcutaneous structures of the body, comprising the steps of:

(a) providing a source of light in a wavelength range of about 0.3 to 1.0 microns;

(b) illuminating a selected portion of the body in at least one of a reflection mode and a transillumination mode with light from said source;

(c) detecting low light levels reflected from or transmitted through said portion of the body, said low light levels having spectral characteristics defined by the relative light absorption properties of subcutaneous structures within said portion of the body;

(d) generating an image of subcutaneous structures within said selected portion of the body;

(e) displaying said image; and (f) wherein the step of detecting low light levels is performed using at least one low level light detection means sensitive to selected wavelength bands within said wavelength range.

18. The method of claim 17 wherein said at least one low level light detection means includes a device selected from the group consisting of an image intensifier tube, a photomultiplier tube, a photodiode and a charge coupled device.

19. A method for enhancing the visualization of veins, arteries or other subcutaneous structures of the body, comprising the steps of:

(a) providing a source of light in a wavelength range of about 0.3 to 1.0 microns;

(b) illuminating a selected portion of the body in at least one of a reflection mode and a transillumination mode with light form said source;

(c) generating an image of subcutaneous structures within said selected portion of the body;

(d) selectively filtering light from said selected portion of the body;

(e) displaying said image; and (f) wherein the steps of generating an image and displaying said image are performed using low level light detection means for detecting low light levels having spectral characteristics defined by the relative light absorption properties of subcutaneous structures within said portion of the body, said low light levels reflected from or transmitted through said portion of the body.

20. The method of claim 19 wherein the step of selectively filtering light reflected from or transmitted through said selected portion of the body is performed using a filter having a narrow passband centered substantially on at least one wavelength selected from the group consisting of about 0.32, 0.345, 0.41, 0.43, 0.455, 0.54, 0.56, 0.58, 0.7, 0.76 and 0.89 microns.

\* \* \* \* \*